United States Patent [19]

Alaimo

[11] 4,381,394

[45] Apr. 26, 1983

[54] 6,7-DICHLORO-2-[(METHYL-2-PYR-ROLIDYLIDENE)AMINO]-4-THI-OCYANATOBENZOTHIAZOLE

[75] Inventor: Robert J. Alaimo, Norwich, N.Y.

[73] Assignee: Norwich Eaton Pharmaceuticals, Inc., Norwich, N.Y.

[21] Appl. No.: 362,898

[22] Filed: Mar. 29, 1982

[51] Int. Cl.³ .................. C01D 31/425; A61K 417/02
[52] U.S. Cl. ..................................... 548/161; 424/270
[58] Field of Search ................. 548/161, 164; 424/270

[56] References Cited

U.S. PATENT DOCUMENTS 4,028,374  6/1977  Pelosi ................................. 548/161

FOREIGN PATENT DOCUMENTS 2152329  4/1972  Fed. Rep. of Germany ...... 548/161

Primary Examiner—Robert Gerstl
Attorney, Agent, or Firm—Anthony J. Franze

[57] ABSTRACT

The compound 6,7-dichloro-2-[(1-methyl-2-pyrrolidylidene)amino]-4-thiocyanatobenzothiazole is useful as an immunomodulating agent.

1 Claim, No Drawings

6,7-DICHLORO-2-[(METHYL-2-PYRROLIDYLIDENE)AMINO]-4-THIOCYANATOBENZOTHIAZOLE

This invention is concerned with chemical compounds and more particularly with the compound 6,7-dichloro-2-[(1-methyl-2-pyrrolidylidene)amino]-4-thiocyanatobenzothiazole useful as an immunomodulating agent.

An immunomodulating agent is a substance which regulates or otherwise affects the immune response of a host. Compounds having such capability are useful as drugs for mitigating the immunological incompetence of a host body often times encountered as an undesired side effect of cancer chemotherapy involving antineoplastic agents. Such depressed immune response lessens the protective function of the immune system permitting the invasion of pathogens such as viruses, bacteria and other parasites which otherwise could be resisted.

The compound of this invention exhibits salutary effect upon the immune system of an animal with respect to resistance to bacterial infection when such system has been depressed by administration of an antineoplastic. Thus, 75% or more of mice administered intraperitoneally 100 mg/kg of cyclophosphamide 4 days before being inoculated intravenously with $1 \times 10^5$ cells of *Pseudomonas aeruginosa* died. In mice not receiving cyclophosphamide, the mortality was about 40%. When the compound of this invention was administered at a level of 20 mg/kg intraperitoneally to cyclophosphamide (100 mg/kg) treated mice at days 4 and 2 before inoculation with *Pseudomonas aeruginosa*, there was a mortality of about 39%.

In order that this invention may be readily available to and understood by those skilled in the art, the currently preferred method for its preparation is set forth as follows:

6,7-Dichloro-2-[(1-methyl-2-pyrrolidylidene)amino]-4-thiocyanatobenzothiazole

To a solution of 2-amino-6,7-dichloro-4-thiocyanatobenzothiazole (55 g, 0.2 mole) in N-methyl pyrrolidinone (500 ml) was added cyanuric chloride (36 g, 0.2 mole) at ice bath temperature. After the addition was complete, the stirred mixture was slowly heated to 80° and held at that temperature for 1 hr. The reaction mixture was then chilled in ice and filtered. The product was heated to a boil in dilute aqueous ammonia then chilled and filtered. The tan product after thorough drying weighed 59 grams (83%).

Recrystallization from methanol/DMF (Darco) provided an analytical sample as white crystals which melted at 151°.

Anal. Calc'd. for $C_{13}H_{10}Cl_2N_4S_2$: C, 43.70; H, 2,83; N, 15.67, Found: C, 43.42; H, 2,78; N, 15.76.

What is claimed is:

1. The compound 6,7-dichloro-2-[(1-methyl-2-pyrrolidylidene)amino]-4-thiocyanatobenzothiazole.

* * * * *